United States Patent
Isono

(10) Patent No.: US 7,306,368 B2
(45) Date of Patent: Dec. 11, 2007

(54) SUPPORT APPARATUS FOR X-RAY DETECTOR

(75) Inventor: Hirotaka Isono, Kyoto (JP)

(73) Assignee: Shimadzu Corporation, Kyoto-fu (JP)

( * ) Notice: Subject to any disclaimer, the term of this patent is extended or adjusted under 35 U.S.C. 154(b) by 0 days.

(21) Appl. No.: 11/480,837

(22) Filed: Jul. 6, 2006

(65) Prior Publication Data
US 2007/0053499 A1 Mar. 8, 2007

(30) Foreign Application Priority Data
Sep. 2, 2005 (JP) ............................ 2005-255731

(51) Int. Cl.
H01J 31/50 (2006.01)
(52) U.S. Cl. ...................... 378/189; 378/181
(58) Field of Classification Search ........ 378/181–183, 378/189, 190, 170, 193, 196, 198, 205
See application file for complete search history.

(56) References Cited
U.S. PATENT DOCUMENTS
6,851,851 B2 * 2/2005 Smith et al. ................ 378/189
7,125,164 B2 * 10/2006 Sekol et al. ................ 378/181
2002/0080921 A1 * 6/2002 Smith et al. ................ 378/189

FOREIGN PATENT DOCUMENTS
JP 5-91993 A 4/1993

* cited by examiner

Primary Examiner—Hoon Song
(74) Attorney, Agent, or Firm—Sughrue Mion, PLLC

(57) ABSTRACT

An X-ray detector support apparatus is adapted to move an X-ray detector in any of six directions along three orthogonal axes, and keep a detection plane of the X-ray detector in either one of vertical and horizontal positions. The detector support apparatus includes a plurality of indicator devices adapted to indicate the movement directions of the detector and associated with corresponding push buttons for designating movement directions. The detector support apparatus is designed to automatically change a relationship between the movement directions and respective indication of the indicator devices, depending on whether the detection plane is kept in the vertical position or in the horizontal position, and controllably move the detector according to the changed relationship. The X-ray detector support apparatus allows an operator to intuitively designate the movement directions of the detector.

4 Claims, 9 Drawing Sheets

Fig. 3

| Detection plane: vertical | | | |
|---|---|---|---|
| Push button switch | Indicator device | Indication | Operation of detector support apparatus |
| 1A | 1H | ↑ | Lifting arm |
| 1B | 1J | → | Retracting arm |
| 1C | 1K | ↓ | Lowering arm |
| 1D | 1L | ← | Stretching arm |
| 1E | 1M | Forward | Moving support column forward |
| 1F | 1N | Rearward | Moving support column rearward |

| Detection plane: horizontal | | | |
|---|---|---|---|
| Push button switch | Indicator device | Indication | Operation of detector support apparatus |
| 1A | 1H | ↑ | Moving support column rearward |
| 1B | 1J | → | Retracting arm |
| 1C | 1K | ↓ | Moving support column rearward |
| 1D | 1L | ← | Stretching arm |
| 1E | 1M | Up | Lifting arm |
| 1F | 1N | Down | Lowering arm |

SUPPORT APPARATUS FOR X-RAY DETECTOR

BACKGROUND OF THE INVENTION

1. Technical Field of the Invention

Aspects of the present invention relate to a diagnostic X-ray radiographic system.

2. Related Art

A related art X-ray detector support apparatus is used in combination with an X-ray tube support apparatus for supporting an X-ray tube unit, and is designed to support an X-ray detector for detecting an X-ray transmitted through a subject after being emitted from the X-ray tube unit and converting the detected X-ray to an electrical signal. As one type of X-ray detector support apparatus, a related art X-ray detector support apparatus may be compatible with radiographic diagnosis in both standing and supine positions, as shown, for example, in FIGS. 7-9. FIG. 8 is an external view showing a manual operation panel of the detector support apparatus illustrated in FIG. 7, and FIG. 9 is a block diagram showing a control unit of the detector support apparatus.

The detector support apparatus 2 illustrated in FIG. 7 comprises a detector holding frame 2A having an X-ray incident surface made of a material such as resin with low X-ray absorptivity. An X-ray detector 3, such as a flat panel-shaped detector, is inserted into and fixedly mounted to the detector holding frame 2A. The detector holding frame 2A includes a manual operation panel 10 fixedly mounted thereon, and a control unit 10P housed therein and including, for example, a microcomputer and a storage device.

When an operator engages a vertical/horizontal-position selector switch 10G (see FIG. 8) in the operation panel 10, the control unit 10P is operable to determine whether the detector holding frame 2A is in a vertical position or in a horizontal position, based on a detection signal from a vertical-position detection section 2N and a horizontal-position detection section 2P (see FIG. 9) housed in an arm 2B and comprising, for example but not by way of limitation, a micro switch. Then, the control unit 10P is operable to command a holding-frame drive section 2L housed in the arm 2B, to allow the detector holding frame 2A to be interchangeably adjusted between the horizontal position (indicated by the dotted line in FIG. 7) and the vertical position (indicated by the solid line in FIG. 7). According to this command, the holding-frame drive section 2L is operable to drive a holding-frame rotating mechanism 2M housed in the arm 2B so as to rotate the detector holding frame 2A about an axis of the arm 2B. Further detailed description of the respective mechanical structures of the detectors, the drive section and the rotating mechanism is omitted.

The detector support apparatus 2 is also designed to move the detector 3 in any of six directions along three orthogonal axes indicated by X-axis, Y-axis and Z-axis in FIG. 7, while keeping the detector 3 in either one of the vertical and horizontal positions. More specifically, for the purpose of the X-axis directional movement, the arm 2B is formed in a telescopic structure, and incorporates an X-axis drive section 2E adapted to operate according to a command from the control unit 10P, and an arm stretching/retracting mechanism 2F adapted to be driven by the X-axis drive section 2E. For the purpose of the Y-axis directional movement, the arm 2B is supported by a support column 2C in a vertically movable manner, and incorporates a Y-axis drive section 2G adapted to operate according to a command from the control unit 10P, and an arm lifting/lowering mechanism 2H adapted to be driven by the Y-axis drive section 2G: For the purpose of the Z-axis directional movement, a base 2D holding the support column 2C is positioned to be movable along a rail 4 laid on a floor, and incorporates a Z-axis drive section 2J adapted to operate according to a command from the control unit 10P, and a support-column moving mechanism 2K adapted to be driven by the Z-axis drive section 2J. Further detailed description of the respective mechanical structures of these drive sections and these mechanisms is omitted.

X-ray image information output from the detector 3 in the form of an electrical signal is entered into an image processing unit (not shown) placed at a remote location, through a cable (not shown) extending through and from inner spaces of the arm 2B, the support column 2C and the base 2D, and a processed image is displayed on a monitor unit (not shown). Further detailed description of these structures is omitted.

The control unit 10P is operable, in response to engaging either one of push button switches 10A, 10B in the operation panel 10, to stretch or retract the arm 2B based on the X-axis drive section 2E and the arm stretching/retracting mechanism 2F. Further, the control of the control unit 10P is operable, in response to engaging either one of push button switches 10C, 10D, to lift or lower the arm 2B based on the Y-axis drive section 2G and the arm lifting/lowering mechanism 2H, and, in response to pushing either one of push button switches 10E, 10F, to move the support column 2C in either one of two directions along the rail 4 based on the Z-axis drive section 2J and the support-column moving mechanism 2K.

In the detector support apparatus 2 is designed to operate as disclosed above, regardless of whether the detector 3 is kept in the vertical position or in the horizontal position, a problem occurs. More specifically, in a detector support apparatus adapted to keep a detection plane of a detector in either one of vertical and horizontal positions, and to move the detector in six directions along three orthogonal axes, if a control circuit and a control program for a control unit are configured such that each of six push buttons for designating movement directions of the detector is fixedly associated with a correspond one of the six directions, and each of the movement directions is indicated on a corresponding one of the push buttons by means of marking (for example but not by way of limitation, engraved or punch mark), an operator has to select one of the push buttons while changing respective definitions of the movement directions fixedly indicated on the respective push buttons, depending on whether the detection plane is kept in the vertical position or in the horizontal position.

As a result, it is difficult to use the related art detector with desired user-friendliness. In this connection, one technique for solving a similar problem to the above is disclosed, for example, in Japanese Patent Laid-Open Publication No. 05-91993 (Patent Publication 1).

SUMMARY OF THE INVENTION

In view of the above, aspects of the exemplary embodiments provide an X-ray detector support apparatus capable of allowing an operator to designate movement directions of a detector more intuitively.

Further, the exemplary embodiment provides an X-ray detector support apparatus, comprising: detector holding means disposed in opposed relation to an X-ray tube, and adapted to hold an X-ray detector for detecting an X-ray transmitted through a subject after being emitted from the X-ray tube and, so as to allow a detection plane of the X-ray detector to be selectively kept in a vertical position and a horizontal position; detector moving means for moving the X-ray detector held by the detector holding means, in any of six directions along three orthogonal axes; input means for manually entering therethrough a command for designating at least either one of the six directions, as a direction in which the X-ray detector is to be moved; control means operable, in response to the command entered from the input means, to output a movement direction of the X-ray detector to the detector moving means so as to instruct the detector moving means to move the X-ray detector in the movement direction; vertical/horizontal-position detecting means for detecting whether the detection plane is kept in the vertical position or in the horizontal position; movement-direction indicating means adapted to indicate a direction in which the X-ray detector is to be controllably moved by the control means in response to the command entered from the input means, and is associated with at least a part of the input means; and storage means for pre-storing information about movement directions of the X-ray detector corresponding to respective commands to be entered from the input means, in both states when the detection plane is in the vertical and horizontal positions.

The control means is operable to determine whether the detection plane is in the vertical position or the horizontal position, based on a detection result of the vertical/horizontal-position detecting means, so as to read the movement directions from the information stored on the storage means based on the determined position of the detection plane and output the read movement directions to the movement-direction indicating means, and, in response to the command entered from the input means, to output a corresponding one of the read movement directions to the detector moving means.

In the X-ray detector support apparatus, the input means includes first input means for manually entering therethrough a command for designating at least either one of four directions along two orthogonal axes included in a plane parallel to the detection plane of the X-ray detector, as a direction in which the X-ray detector is to be moved, and second input means for manually entering therethrough a command for designating at least either one of two directions along one axis perpendicular to the detection plane, as a direction in which the X-ray detector is to be moved, wherein the first input means and the second input means are arranged in a substantially segmented manner.

As above, in the detector support apparatus adapted to keep the detection plane in either one of the vertical and horizontal positions and move the detector in any of the six directions along the three orthogonal axes, the exemplary embodiment allows an operator to intuitively recognize a relationship between movement directions of the detector and push buttons for designating the movement directions, regardless of whether the detection the X-ray detector is in the vertical position or in the horizontal position, to facilitate the manual operation of the detector support apparatus.

BRIEF DESCRIPTION OF THE DRAWINGS

Exemplary embodiments will be more apparent from the following detailed description taken in conjunction with the accompanying drawings, in which:

FIG. 3 is a table showing respective indications of indicator devices corresponding to respective buttons and the operations of the X-ray detector support apparatus according to the exemplary embodiment;

DETAILED DESCRIPTION OF THE EXEMPLARY EMBODIMENTS

Figure 1:
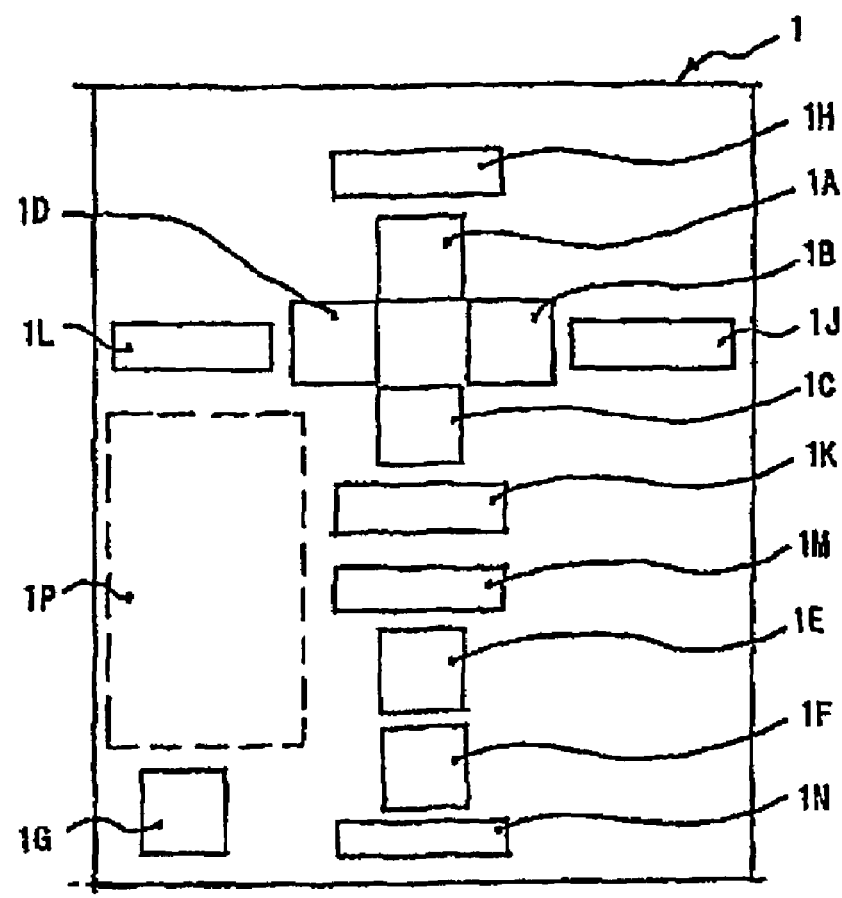
FIG. 1 illustrates a manual operation panel of an X-ray detector support apparatus according to one exemplary embodiment.

Hereinafter, exemplary embodiments will be described in detail with reference to the accompanying drawings. The aspects and features of the present invention and methods for achieving the aspects and features will be apparent by referring to the embodiments to be described in detail with reference to the accompanying drawings. However, the present invention is not limited to the exemplary embodiments disclosed hereinafter, but will be implemented in diverse forms. The matters defined in the description, such as the detailed construction and elements, are nothing but specific details provided to assist those of ordinary skill in the art in a comprehensive understanding of the exemplary embodiments, as defined within the scope of appended claims. In the detailed description, the same drawing reference numerals are used for the same elements across various figures.

Figure 2:
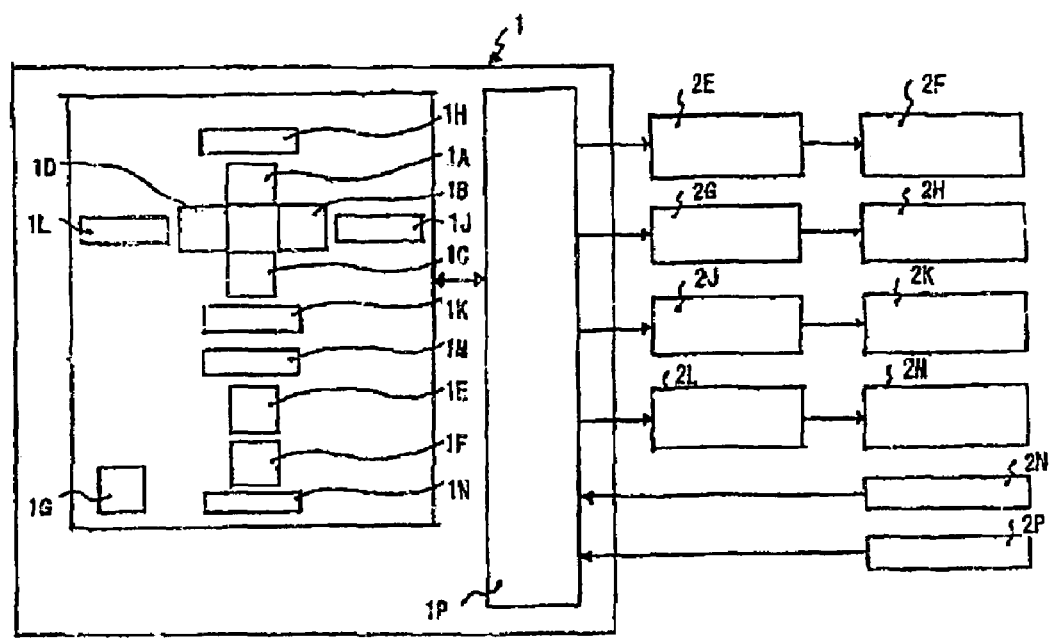
FIG. 2 is a block diagram showing a control system of the X-ray detector support apparatus according to the exemplary embodiment.
Figure 4:
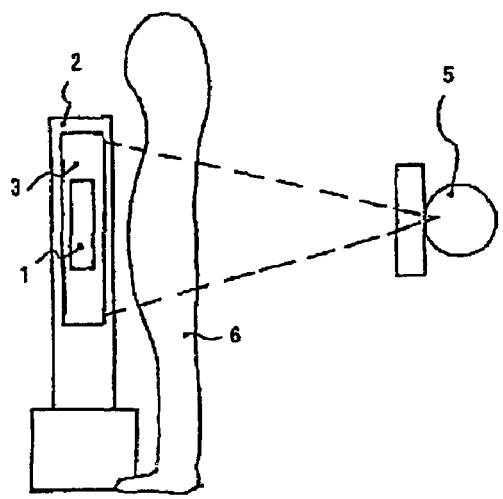
FIGS. 4A to 4C are explanatory diagrams showing an indication mode of the operation panel, during radiographic diagnosis in a standing position using the X-ray detector support apparatus, according to the exemplary embodiment.
Figure 4:
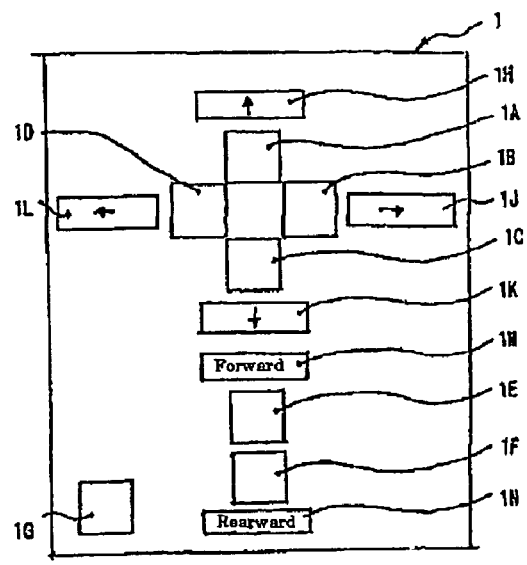
Figure 4:
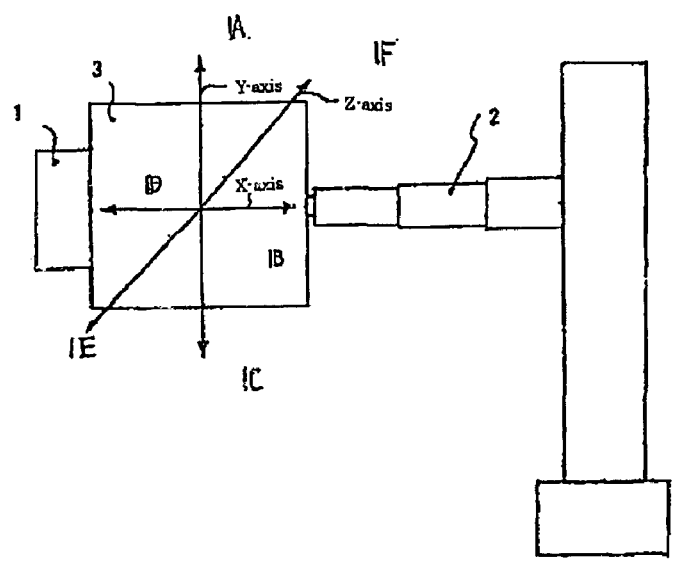

FIG. 1 shows a manual operation panel of an X-ray detector support apparatus according to the exemplary embodiment, and FIG. 2 shows a control system of the X-ray detector support apparatus. The manual operation panel 1 of the X-ray detector support apparatus according to this exemplary embodiment is fixedly mounted to the detector holding frame 2A illustrated in FIG. 7 in place of the manual operation panel 10. The operation panel 1 has N (for example, but not by way of limitation, 6) push button switches 1A, 1B, 1C, 1D, 1E, 1F for designating movement directions of an X-ray detector, and N (for example, but not by way of limitation, 6) indicator devices 1H, 1J, 1K, 1L, 1M, 1N each adapted to indicate a visual indicator such as a character, numeral or graphic on a corresponding one of the push button switches. For example, each of the indicator devices may include a diode indicator.

The operation panel 1 further includes a vertical/horizontal-position selector switch 1G having the substantially same function as that of the vertical/horizontal-position selector switch 10G of the aforementioned detector support apparatus 2. More specifically, when an operator pushes the vertical/horizontal-position selector switch 10G; a control unit 1P incorporated in the operation panel 1 and including, for example, a microcomputer and a storage device, is operable to rotate the detector holding frame 2A about an axis of an arm 2A, in such a manner as that the detector holding frame 2A is movable between a horizontal position and a vertical position. The X-ray detector support apparatus includes a holding-frame drive section 2L, a holding-frame rotating mechanism 2M, a vertical-position detection section 2N and a horizontal-position detection section 2P, each of which has the substantially same function as that of a corresponding one of the components of the aforementioned detector support apparatus 2, and their description will be omitted herein.

FIG. 3 is a table showing respective indications of the indicator devices 1H, 1J, 1K, 1L, 1M, 1N corresponding to the respective push button switches 1A, 1B, 1C, 1D, 1E, 1F, and an operation of the detector support apparatus 2 in response to pushing each of the N (e.g., 6) push button switches, in both states when a detection plane of a detector 3 is kept in a vertical position and in a horizontal position. These relationships between each of the indications of the indicator devices and each of the operations of the detector support apparatus 2 are pre-stored on the storage device, such as ROM (read-only memory) but not limited thereto, of the control unit 1P.

Figure 7:
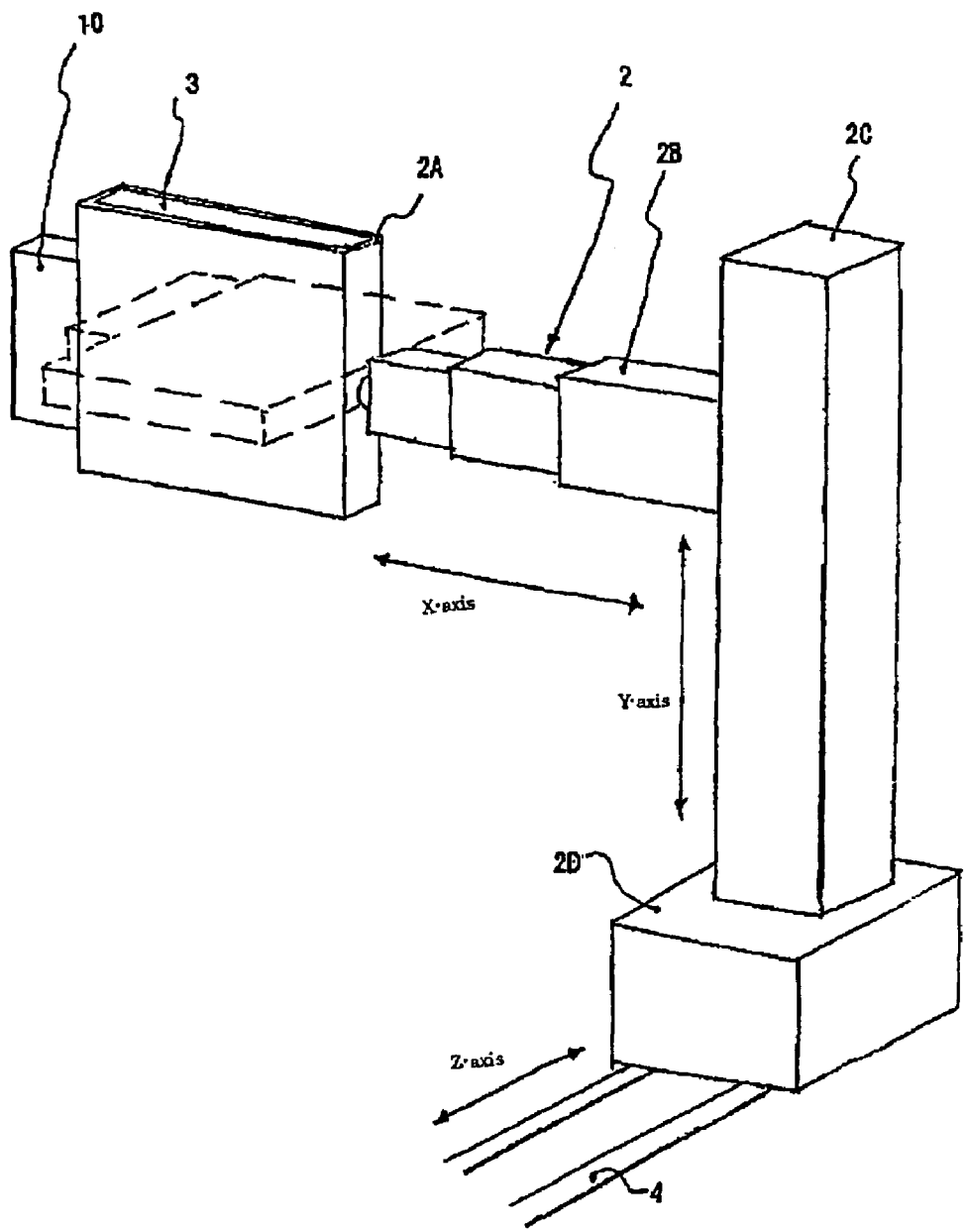
FIG. 7 is an explanatory diagram showing an X-ray detector support apparatus.
Figure 8:
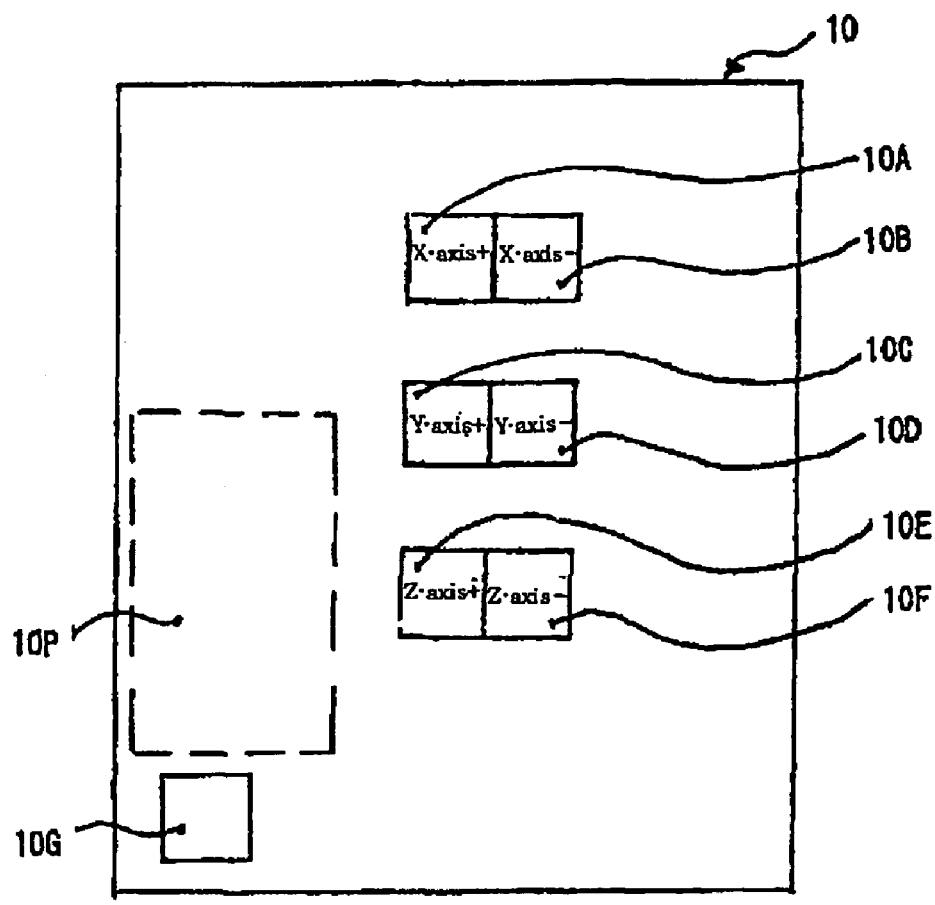
FIG. 8 an explanatory diagram showing a manual operation panel of an X-ray detector support apparatus as a comparative example.
Figure 9:
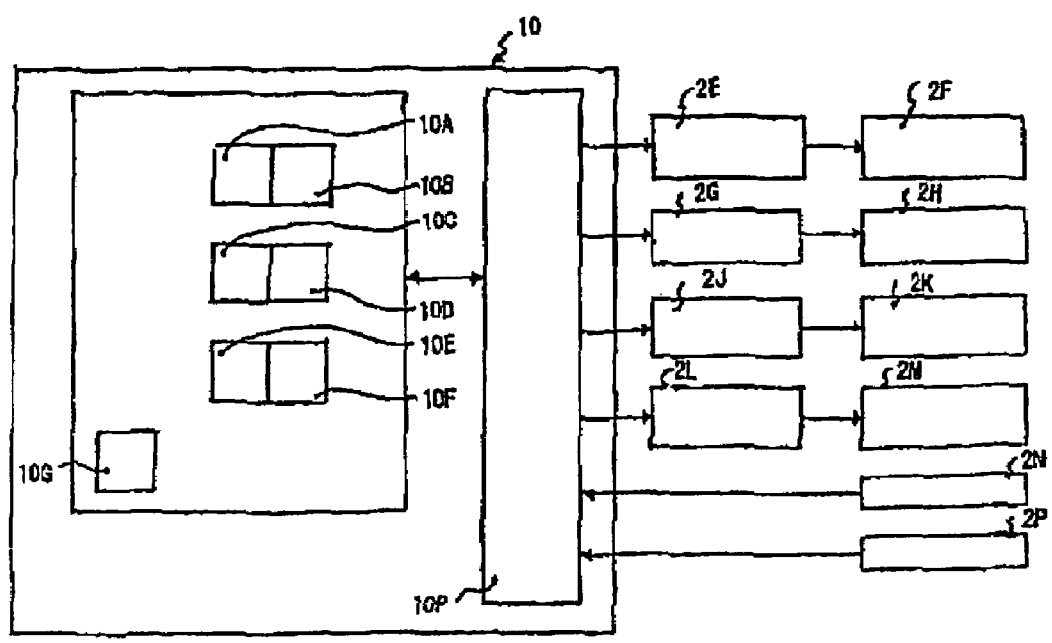
FIG. 9 is a block diagram showing a control system of the X-ray detector support apparatus in FIG. 8.

With reference to FIGS. 4A to 5C, the movement of the detector 3 during radiographic diagnosis in standing and supine positions is described below. In FIGS. 4A to 5C, the same component or unit as that in FIG. 1 or 7 is defined by the same reference numeral or code, and its description will be omitted.

FIG. 4A shows a positional relationship of the detector support apparatus 2, the detector 3, the operation panel 1, a subject 6 and an X-ray tube unit 5, during radiographic diagnosis in the standing position. FIG. 4B shows a positional relationship of the detector support apparatus 2, the detector 3 and the operation panel 1, when viewed from the side of the subject 6, together with N (e.g., 6) directions along N/2 (e.g., 3) axes, in which the detector 3 is movable. FIG. 4C shows one example of indications of the indicator devices 1H, 1J, 1K, 1L, 1M, 1N on the operation panel 1. However, the exemplary embodiment is not limited thereto. In FIG. 4A, an X-ray tube support apparatus for supporting the X-ray tube unit 5 is omitted.

When the push button switch 1A or 1C on the operation panel 1 is pushed during radiographic diagnosis in the standing position as shown in FIG. 4A, the control unit 1P incorporated in the operation panel 1 is operable, based on the information stored on the storage device built in the control unit 1P, as shown in FIG. 3, to instruct a Y-axis drive section 2G and an arm lifting/lowering mechanism 2H to lift or lower the arm 2A. When the push button switch 1B or 1D is pushed, the control unit 1P is operable to instruct an X-axis drive section 2E and an arm stretching/retracting mechanism 2F to retract or stretch the arm 2A. While the detector 3 will be moved in conjunction with the above operations, such a movement will occur within the same plane as the current detection plane of the detector 3. Thus, in the radiographic diagnosis in the standing position, the control unit 1P is operable to indicate arrows representing respective ones of M (e.g., 4) directions along M/2 (e.g., 2) axes, on the indicator devices 1H, 1J, 1K, 1L, as shown in FIG. 4C, so as to allow an operator to viscerally recognize the movement directions. When the push button switch 1E or 1F is pushed, the control unit 1P is operable to instruct a Z-axis drive section 2J and a support-column moving mechanism 2K to move a support column 2C in either one of two directions along a rail 4.

In conjunction with this operation, the detector 3 will be moved in a direction substantially perpendicular to the detection plane, or moved forward or rearward when viewed from the side of the operator. Such movement directions are indicated on the indicator devices using arrows or other indication signs. Thus, character "forward" or "rearward" may be indicated on a corresponding one of the indicator devices 1M, 1N. These indications will be maintained in the N (e.g., 6) indicator devices 1H, 1J, 1K, 1L, 1M, 1N, until the detector 3 or its detection plane is changed from the current vertical position to the horizontal position.

Figure 5A:
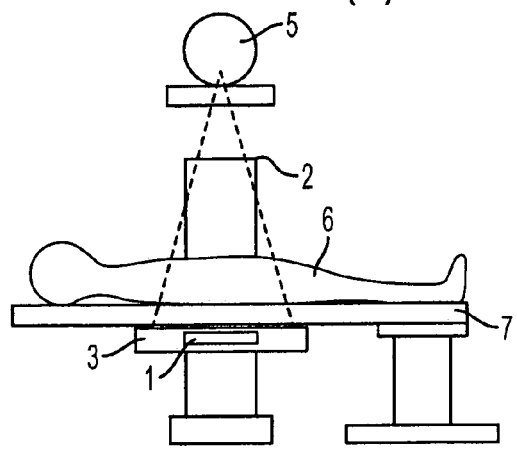
FIGS. 5A to 5C are explanatory diagrams showing an indication mode of the operation panel, during radiographic diagnosis in a supine position using the X-ray detector support apparatus, according to the exemplary embodiment.
Figure 5B:
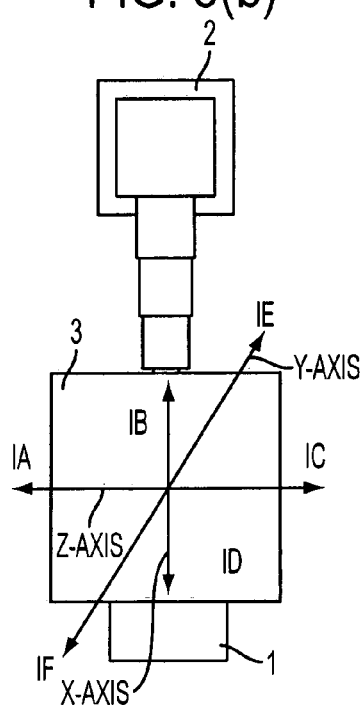
Figure 5C:
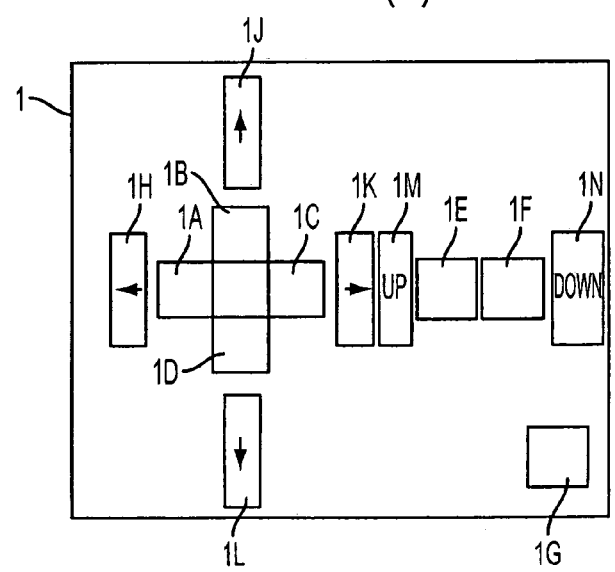

When the push button switch 1A or 1C of the operation panel 1 is pushed during radiographic diagnosis in the supine position as shown in FIG. 5A, the control unit 1P incorporated in the operation panel 1 is operable, based on the information stored on the storage device built in the control unit 1P, as shown in FIG. 3, to instruct the Z-axis drive section 2J and the support-column moving mechanism 2K to move the support column 2C toward the head or legs of a subject 6, positioned on a bed portion 7, along the rail 4. When the push button switch 1B or 1D is pushed, the control unit 1P is operable to instruct the X-axis drive section 2E and the arm stretching/retracting mechanism 2F to retract or stretch the arm 2A. The movement of the detector 3 in conjunction with the above operation occurs within the substantially same plane as the current detection plane of the detector 3. Thus, in radiographic diagnosis in the supine position, the control unit 1P is operable to indicate arrows representing respective ones of M (e.g., 4) directions along M/2 (e.g., 2) axes, on the indicator devices 1H, 1J, 1K, 1L, as shown in FIG. 5C, so as to allow an operator to viscerally recognize the movement direction. When the push button switch 1E or 1F is pushed, the control unit 1P is operable to instruct the Y-axis drive section 2G and the arm lifting/lowering mechanism 2H to lift or lower the arm B. The movement of the detector 3 in conjunction with the above operation will occur in a direction substantially perpendicular to the detection plane, i. e. the detector 3 is moved upward or downward when viewed from the side of the operator. Such movement directions are indicated on the indicator devices using arrows or other indicative signs. Thus, character "up" or "down" may be indicated on a corresponding one of the indicator devices 1M, 1N. These indications are maintained in the N (e.g., 6) indicator devices 1H, 1J, 1K, 1L, 1M, 1N, until the detector 3 is changed from the current horizontal position to the vertical position.

As above, when an operator intends to move the detector 3 in either one of M (e.g., 4) directions along M/2 (e.g., 2) orthogonal axes included in the current detection plane of the detector 3, the detector support apparatus according to this exemplary embodiment allows the operator to viscerally select either one of the push button switches 1A, 1B, 1C, 1D according to the arrowed direction indicated on a corresponding one of the indicator devices 1H, 1J, 1K, 1L, irrespective of whether the detection plane is kept in the vertical position or in the horizontal position. Further, when the operator intends to move the detector 3 in either one of X (e.g., 2) directions along X/2 (e.g., 1) axis perpendicular to the current detection plane, the detector support apparatus according to this exemplary embodiment allows the operator to viscerally select either one of the push button switches 1E, 1F according to the indication on a corresponding one of the indicator devices 1M, 1N.

While the operation panel 1 in the above exemplary embodiment is mounted to the detector holding frame 2A, the exemplary embodiment may be applied to an X-ray radiographic system where a manual operation panel 1 is disposed separately from or independently of the detector holding frame 2A, or an X-ray radiographic system where a manual operation panel 1 is integrated with another manual operation panel, such as an manual operation panel of the X-ray tube support apparatus.

In the above exemplary embodiment, irrespective of whether the detector 3 is kept in the vertical position or in the horizontal position, the indication of each of the indicator devices 1H, 1J, 1K, 1L is substantially the same. Thus, instead of these indicator devices, a symbol, such as an arrow, representing the movement direction, may be marked in each of the corresponding push button switches.

While each of the indicator devices 1H, 1J, 1K, 1L in the above exemplary embodiment is designed to indicate the arrow representing a given movement direction, any suitable indicator (e.g., character) may be used for indicating the movement direction. Further, while each of the indicator devices 1M, 1N in the above embodiment is designed to indicate the characters "forward" and "rearward" when the detection plane is kept in the vertical position, and the characters "up" and "down" when the detection plane is kept in the horizontal position, the exemplary embodiment is not limited to these indicators, but any other suitable expression or sign easily recognizable to an operator may be used.

Further, the arrangement of the (e.g., 6) push button switches 1A, 1B, 1C, 1D, 1E, 1F and the indicator devices 1H, 1J, 1K, 1L, 1M, 1N is not limited to that as shown in FIG: 1, and any other suitable arrangement easy to handle for an operator may be used.

Figure 6:
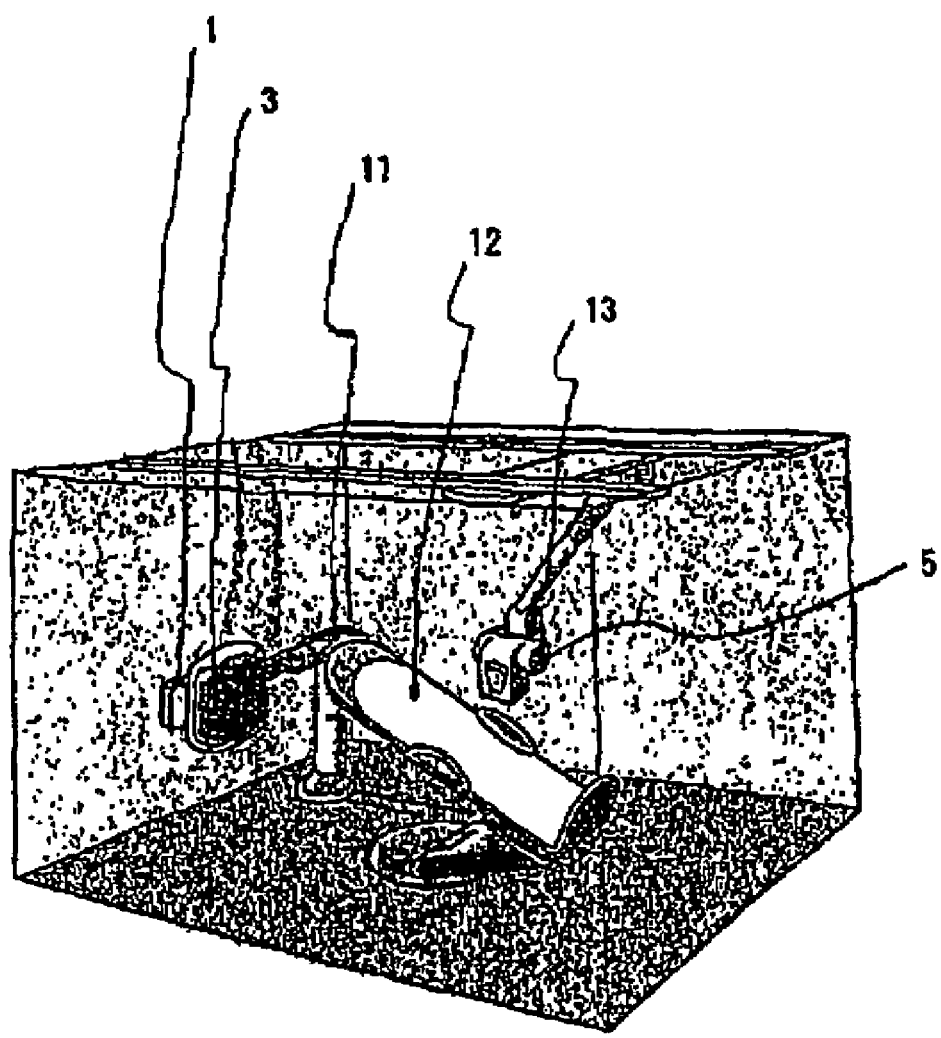
FIG. 6 is an explanatory diagram showing an exemplary, non-limiting radiographic system configured to use an X-ray detector support apparatus as a normal X-ray detector support apparatus and additionally as a bed for radiographic diagnosis, according to the exemplary embodiment.

FIG. 6 is an explanatory diagram showing one example of a radiographic system equipped with an X-ray detector support apparatus usable as a normal X-ray detector support apparatus and additionally as a bed for radiographic diagnosis in a supine position, according to the exemplary embodiment. In this system, an X-ray detector support apparatus 11 has the substantially same functions as those of the X-ray detector support apparatus 2, and a bed portion 12 is kept in a substantially horizontal position when the system is used for radiographic diagnosis in the supine position. Further, when the X-ray detector support apparatus 11 is used in a radiographic diagnosis in the standing position, the bed portion 12 is kept in a substantially vertical position and moved toward a fixed reference, such as a room wall (but not limited thereto). Moreover, the bed portion 12 illustrated in FIG. 6 and the bed portion 7 illustrated in FIG. 5A may be substantially similar, but such a correlation therebetween is not necessary.

An X-ray tube support apparatus 13 is designed to allow an X-ray tube unit 5 to be disposed at a position opposed to a detector 3 supported by the detector support apparatus 11, in the above two modes. The X-ray tube unit 5, a subject and the detector 3 in this system is arranged in the substantially same manner as those illustrated in FIGS. 4A and 4B. The exemplary embodiment may be applied to the detector support apparatus 11 and a manual operation panel 1 as a component thereof.

The foregoing exemplary embodiment is not limited to an X-ray support apparatus, and may be directed to any target tissue detection device. Further, the support structure is not limited to a X-ray support structure, and may be directed to any target tissue detection device that has a support that is movable upon at least one axis, and optionally two or three axes that are orthogonal with respect to each other.

Further, the exemplary embodiments may include a computer-readable medium having a set of instructions configured to perform operations directed to the movement of the foregoing support structure in response to a command received based on user input to the operation panel.

Although exemplary embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. An X-ray detector support apparatus, comprising:
   detector holding means, disposed in opposed relation to an X-ray tube and adapted to hold an X-ray detector, for detecting an X-ray transmitted through a subject after being emitted from said X-ray tube and, such that a detection plane of said X-ray detector is configured to be selectively maintained in one of a vertical position and a horizontal position;
   detector moving means for moving said X-ray detector held by said detector holding means, in any of a plurality of N directions along N/2 orthogonal axes;
   input means for manually entering therethrough a command for designating at least one of said N directions, as a direction in which said X-ray detector is to be moved;
   control means operable, in response to the command entered from said input means, for outputting a movement direction of said X-ray detector to said detector moving means, so as to instruct said detector moving means to move said X-ray detector in said movement direction;
   vertical/horizontal-position detecting means for detecting whether said detection plane is being maintained in the vertical position or in the horizontal position;
   movement-direction indicating means for indicating a direction in which said X-ray detector is controllably movable by said control means in response to the command entered from said input means, said movement-direction indicating means being associated with at least a part of said input means; and
   storage means for pre-storing information about movement directions of said X-ray detector corresponding to respective commands to be entered from said input means, when said detection plane is in both of the vertical and horizontal positions,
   wherein said control means is operable to determine whether said detection plane is in the vertical position or the horizontal position based on a detection result of said vertical/horizontal-position detecting means, so as to read the movement directions from the information stored on said storage means based on said determined position of the detection plane, and output said read movement directions to said movement-direction indicating means, and, in response to the command entered from said input means, to output a corresponding one of said read movement directions to said detector moving means.

2. The X-ray detector support apparatus as defined in claim 1, wherein said input means includes first input means for manually entering therethrough a command for designating at least either one of M directions along M/2 orthogonal axes included in a plane parallel to said detection plane of said X-ray detector, as a direction in which said X-ray detector is to be moved, and second input means for manually entering therethrough a command for designating at least either one of X directions along X/2 axis perpendicular to said detection plane, as a direction in which said X-ray detector is to be moved, wherein said first input means and said second input means are arranged in a segmented manner.

3. The apparatus of claim 1, wherein N is 6.

4. The apparatus of claim 2, wherein M is 4 and X is 2.

* * * * *